United States Patent [19]

Franklin

[11] Patent Number: 4,923,795
[45] Date of Patent: May 8, 1990

[54] FLEXIBLE LOWER ARTIFICIAL DENTURE

[76] Inventor: Scott B. Franklin, 919 SW. Taylor, #512, Portland, Oreg. 97205

[21] Appl. No.: 185,484

[22] Filed: Apr. 25, 1988

[51] Int. Cl.⁵ .......................................... A61C 13/02
[52] U.S. Cl. ................................. 433/168.1; 433/169
[58] Field of Search ................... 433/167, 168.1, 169, 433/171, 172, 177, 180

[56] References Cited

U.S. PATENT DOCUMENTS

| | | | |
|---|---|---|---|
| 2,266,478 | 12/1941 | Snell | 433/177 |
| 2,277,370 | 3/1942 | Sheedy . | |
| 2,664,631 | 1/1954 | Hollander et al. | 433/168.1 |
| 2,770,880 | 11/1956 | Sherrod | 433/177 |
| 2,896,324 | 7/1959 | Plotnick . | |
| 2,911,720 | 11/1959 | Greenmun . | |
| 3,813,778 | 6/1974 | Van Handel . | |
| 3,837,079 | 9/1974 | Cecero | 433/177 |
| 3,921,293 | 11/1975 | Kemmurdji . | |
| 4,634,381 | 1/1987 | Kusano et al. . | |
| 4,654,006 | 3/1987 | Kusano et al. . | |

FOREIGN PATENT DOCUMENTS

| | | | |
|---|---|---|---|
| 478581 | 6/1929 | Fed. Rep. of Germany | 433/177 |
| 736805 | 9/1955 | United Kingdom | 433/169 |

Primary Examiner—Robert P. Swiatek
Assistant Examiner—Nicholas D. Lucchesi
Attorney, Agent, or Firm—Eugene M. Eckelman

[57] ABSTRACT

A pair of denture sections have curved front and side portions cooperating to form a U-shape to fit the lower jaw of a person. Front edges of the sections are disposed adjacent each other and between two front teeth and a bottom layer of resilient material is bonded integrally to both sections. A front reinforced portion of resilient material connects the sections together into an integral unit. The resilient connection allows the sections to adjust relative to each other to compensate for distortion of the gums during chewing, and a flexible torsion bar is connected across the front edges in an area through a reinforcing portion of the resilient material whereby to reinforce the connection and yet to allow the adjustable movement of the sections.

8 Claims, 1 Drawing Sheet

FLEXIBLE LOWER ARTIFICIAL DENTURE

BACKGROUND OF THE INVENTION

This invention relates to new and useful improvements in flexible lower artificial dentures.

Artificial dentures have heretofore been known that are provided with adjusting means which allow one section of the denture to adjust relative to the other section for the purpose of independent movement between the sections during chewing. For example, U.S. Pat. No. 2,277,370 illustrates a bisectional lower denture connected together at the front by screw means which permit angular movement between the sections about the axis of the screw. U.S. Pat. No. 2,911,720 shows a bisectional denture utilizing a leaf spring as a holding device and also employing a travel stop. U.S. Pat. No. 2,896,324 is directed to an artificial denture having a bridge portion capable of adjustable movement resulting from chewing forces (of mastication). Other patents, such as U.S. Pat. Nos. 3,813,778, 3,921,293 and 4,634,381 show dentures having a resilient support for accomplishing comfort and/or flexing relative to the gums or other parts of the denture.

It has also heretofore been known to provide artificial dentures with a bottom layer of resilient material on a rigid body portion of the denture whereby to add comfort to the support on the wearer's gums. Such a resilient layer is shown in U.S. Pat. No. 4,654,006.

SUMMARY OF THE INVENTION

According to the present invention and forming a primary objective thereof, a flexible lower artificial denture is provided which has improved features of comfort, improved features of fit in the wearer's mouth, and improved adjusting features for chewing functions over those of the prior disclosures, and more particularly a denture of the type described utilizing a novel structure of a two-piece base structure with a resilient bottom layer which serves to connect the two base sections together and also to provide comfort for the wearer as well as to provide automatic adjustment of the two sections relative to each other.

Another object of the invention is to provide a flexible lower artificial denture employing flexible torsion means in combination with the resilient layer on the bottom of the denture sections whereby to provide a positive and secured connection of the sections together and positive return of the sections to a rest position and at the same time to allow adjustable flexing of the two sections relative to each other accomplished by the resilient material.

In carrying out these objectives, the denture includes a pair of cooperating rigid denture base sections each having a curved front portion and a side extension. The sections form a U-shape which is molded to the shape of the alveolar ridge of each person's lower jaw. The two sections have front edges disposed adjacent each other between two front teeth. A bottom layer of resilient material is chemically bonded integrally to the sections and between portions of the disconnected front edges whereby to connect the sections together into an integral unit at the front and to allow the sections to adjust relative to each other to compensate for distortion of the gums during chewing. In a preferred structure, flexible torsion means are provided which extend laterally across the disconnected front edges and through a thickened portion of the resilient material and have opposite ends thereof anchored in the respective rigid base sections. The resilient layer and torsion means connect the sections together into an integral unit but allow the sections to adjust relative to each other to compensate for distortions of the gums.

The invention will be better understood and additional objects and advantages will become apparent from the following description taken in connection with the accompanying drawings.

DETAILED DESCRIPTION OF A PREFERRED EMBODIMENT

Figure 1:
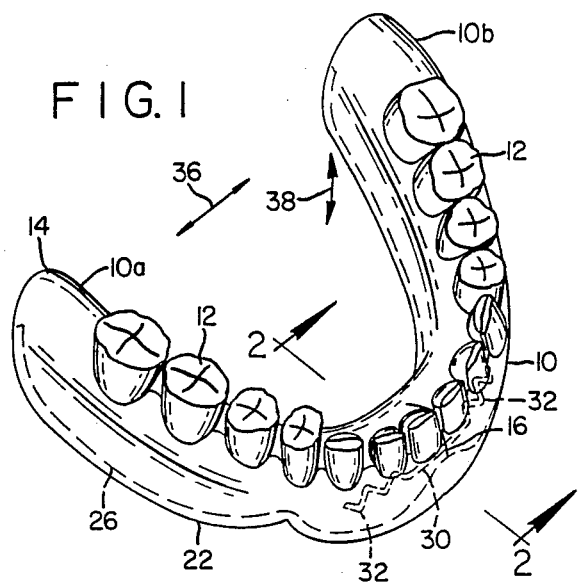
FIG. 1 is a perspective view of a flexible lower artificial denture embodying features of the invention.

With particular reference to the drawings, the invention comprises an artificial denture 10 consisting of two sections 10a and 10b. These sections are constructed of well-known material which when set is rigid, such as a suitable acrylic resin, and integrally support artificial teeth 12 along their upper surfaces in a well-known custom molded manner for each patient. The lower surface 10c of the sections is contoured to fit the gums and as usual has rearward ends 14 capable of resting directly on the retromolar pad of the lower jaw. The front edges 16 of the denture sections extend downwardly between two front teeth of the sections. Such edges are closely adjacent to each other and in abutting relation in the rest condition of the denture. These edges are substantially vertical in their upper portion but have recessed or backcut lower portions 18 leading into the bottom surface 10c of the denture sections.

The bottom of the denture sections is lined with a layer of resilient material 22 of a well-known type chemically bonded thereto, such as an Olefin thermoplastic elastomer, as in U.S. Pat. No. 4,654,006, serving to provide cushioning comfort to the wearer. This layer of resilient material covers the entire bottom surface of the denture sections with the exception of the very rearward ends 14, such unlined end portions engaging directly, as stated, with the retromolar pads of the jaw as is common practice. Layer 22 extends outwardly and inwardly around the bottom defining edges of the sections and terminates in a feathered edge 26 a short distance up the outer and inner sides. Resilient material 22 also fills in the recessed or backcut portions 18 at the front, FIGS. 2–4, to form a reinforcing front portion 28 of resilient plastic. Such reinforcing portion connects the two sections together and at the same time allows yieldable movement of the two sections relative to each other. Such relative movement yields to forces of chewing in many directions to provide comfort and better chewing functions for the person wearing the dentures, as will be described in greater detail hereinafter.

Figure 2:
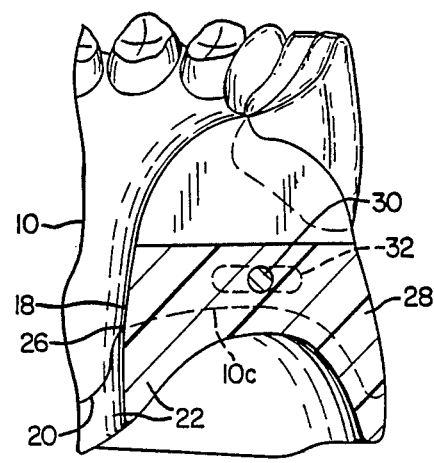
FIG. 2 is an enlarged cross sectional view taken on the line 2—2 of FIG. 1 comprising a center line between the two denture sections.
Figure 3:
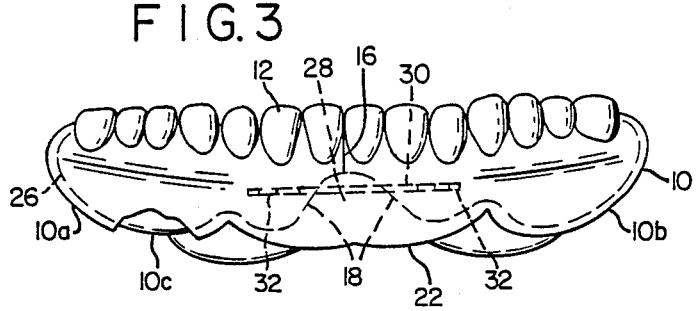
FIG. 3 is a front elevational view of the denture in a rest or normal position.
Figure 4:
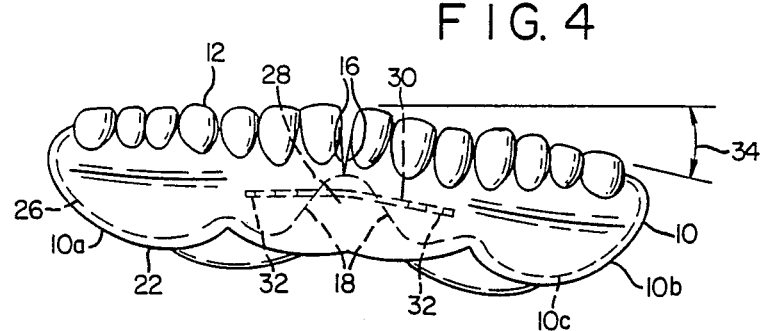
FIG. 4 is a view similar to FIG. 3 but showing one of the adjusted positions of the denture sections caused by uneven chewing forces.
Figure 5:
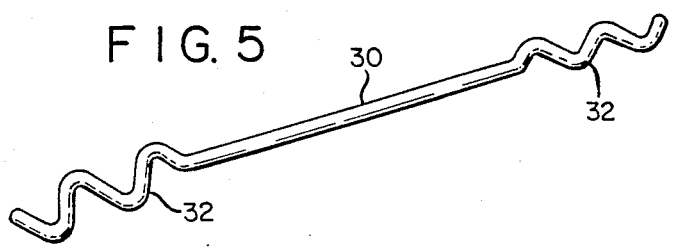
FIG. 5 is a perspective view of flexible torsion means apart from the denture sections.

In a preferred construction, a flexible torsion bar 30 is molded integrally at its ends in the front of the respective denture sections 10a and 10b with an intermediate portion thereof passing through the recessed area centrally between the two sections defined by the cutback edges 1B. Since this area contains the resilient material 22, bar 30 extends through such material. The bar has end zig zag portions 32, FIG. 5, embedded in the hard plastic of the respective base sections. These zig zag portions are formed in a flat plane, as best seen in FIGS. 2–4. Thus, the bar is securely anchored longitudinally and against rotation as well.

Bar 30 is constructed of a rugged flexible material such as spring steel or Plastic and preferably is round in cross section whereby one denture section can adjust resiliently relative to the other. Furthermore, the bar 30 is of a construction such that with the ends thereof securely anchored against rotation in the hard plastic the portion between the ends can twist resiliently on on axis of the bar to allow for torsional adjustment. Furthermore, the construction of the torsion bar 30 is such that it has a memory in all directions and is engineered to have a strength such that although it allows one denture section to immediately adjust during chewing functions, it will positively return such section to a rest position when the forces subside. The position of the bar 50 in its embedded depth down from the top of the resilient material 22 at the center is such that it provides a good leverage for returning one or both denture sections to a rest position but at the same time it efficiently allows relative adjustable movement of the sections.

According to the invention, the lower denture, with the resilient layer 22 on the bottom surface provides a comfort fit on the gums. The tissue surface is seamless and thus there are no edges or other abnormalities in the tissue engaging surface. With the flexible connection of the sections, one section can adjust relative to the other whereby when one section moves downwardly or twists as a result of uneven chewing forces, it will not affect the seated engagement of the other section on the gum tissue.

In particular, the connection between the sections, accomplished by the resilient layer 22 and the torsion bar 30 allows the following adjustments and combinations thereof: With reference to FIG. 4, one section can pivot downwardly relative to the other section as shown by arrows 34. Also, the rearward ends 14 can move toward each other or away from each other, as indicated by arrows 36 in FIG. 1. Moving them together may be beneficial for efficiently engaging lingual posterior portions of the mandible which have undercuts. Further yet, the rearward end of a section can pivot upwardly or downwardly as shown by arrows 38 in FIG. 1, comprising a torsional movement and force on the bar 30 and reinforcing portion 28. In all cases the one section is returned to the rest position when not influenced by chewing forces.

The present denture thus provides a comfortable fit and one side can react to all forces of chewing without affecting the other side. In view of its structural flexibility it reacts to substantially all types of chewing such as vertical, rolling, sliding, etc. The strength and flexibility of the torsion bar needs to assist in returning the sections to their rest position but its characteristics should have minimum resistance to flexing of the sections.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A lower artificial denture comprising:
   a pair of cooperating rigid denture base sections having upper and lower surfaces,
   said sections each having a curved front portion and a side extension with defining side surfaces,
   said sections cooperating to form a U-shape to correspond to the shape of the ridge of a person's lower jaw and having (front) facing edges disposed closely adjacent each other throughout their length in disconnected relation,
   the lower surface of said sections being contoured to fit over the lower gums of a person,
   and a lower layer of resilient material bonded integrally to said sections including the area across said disconnected front edges of said sections,
   said layer of resilient material connecting said sections together into an integral unit at the front and also providing a bottom seamless surface across said disconnected front edges,
   said resilient layer across said seamless surface comprising the sole connection between said sections and allowing said sections to adjust relative to each other to compensate for distortion of the gums during chewing.

2. The artificial denture of claim 1 wherein said facing edges are recessed laterally in a lower portion thereof and said lower resilient layer covers a principal portion of the lower surface of said sections and extends into said front edge recesses providing a reinforced connecting portion for said sections.

3. The artificial denture of claim 2 including a flexible connecting bar having opposite ends anchored in respective sections and spanning across said disconnected front edges, said bar also connecting said sections together and allowing said sections otherwise to flex with said layer of resilient material.

4. The artificial denture of claim 2 including a flexible connecting bar having opposite ends anchored in respective sections and spanning across said disconnected front edges, said bar extending through said reinforced connecting portion of said resilient layer and also holding said sections together and allowing said sections otherwise to flex with said layer of resilient material.

5. A lower artificial denture comprising:
   a pair of cooperating rigid denture base sections having upper and lower surfaces,
   said sections each having a curved front portion and a side extension with defining side surfaces,
   said sections cooperating to form a U-shape to correspond to the shape of the ridge of a person's lower jaw and having front edges disposed closely adjacent each other in disconnected relation,
   the lower surface of said sections being contoured to fit over the lower gums of a person,
   a lower layer of resilient material bonded integrally to said sections including the area across said disconnected front edges of said sections and providing a seamless surface across said disconnected edges,
   and one piece flexible torsion means extending laterally across said disconnected front edges and having opposite ends anchored in respective sections and extending through a portion of said resilient layer, said resilient layer and torsion means connecting said sections together into an integral unit at the front and allowing said sections to adjust relative to each other to compensate for distortion of the gums during chewing.

6. The artificial denture of claim 5 wherein said flexible torsion means comprises a flexible torsion bar.

7. The artificial denture of claim 5 wherein said flexible torsion means comprises a flexible torsion bar having zig zag ends embedded in said respective sections in a flat plane to anchor the bar against rotation.

8. The artificial denture of claim 5 wherein said front edges are recessed laterally in a lower portion thereof and said lower resilient layer covers a principal portion of the bottom surface of said sections and extends into said front edge recesses providing a connecting portion for said sections, said flexible torsion means comprising a flexible torsion bar and extending through a portion of said resilient layer.

* * * * *